United States Patent [19]

Chubachi

[11] Patent Number: 4,492,117
[45] Date of Patent: Jan. 8, 1985

[54] ULTRASONIC NONDESTRUCTIVE TEST APPARATUS

[75] Inventor: Noriyoshi Chubachi, Miyagi, Japan

[73] Assignee: Keisuke Honda, Aichi, Japan

[21] Appl. No.: 439,581

[22] Filed: Nov. 5, 1982

[30] Foreign Application Priority Data

Nov. 13, 1981 [JP] Japan ................................ 56-182709

[51] Int. Cl.³ ............................................ G01N 29/00
[52] U.S. Cl. ...................................... 73/597; 73/644; 367/113
[58] Field of Search ................... 73/597, 644; 367/113

[56] References Cited

U.S. PATENT DOCUMENTS 3,519,985 7/1970 Page ..................................... 367/113
3,690,155 9/1972 Eichler ................................. 73/597

FOREIGN PATENT DOCUMENTS 892290 12/1981 U.S.S.R. ................................ 73/597

Primary Examiner—Howard A. Birmiel
Attorney, Agent, or Firm—Burgess, Ryan & Wayne

[57] ABSTRACT

An ultrasonic transmitting element and an ultrasonic receiving element are arranged in a sample liquid in opposition to each other. Either the ultrasonic transmitting element or the ultrasonic receiving element is finely vibrated, and the difference between the velocities of sound in the sample liquid and another sample in the sample liquid is displayed on a CRT.

6 Claims, 8 Drawing Figures

ULTRASONIC NONDESTRUCTIVE TEST APPARATUS

BACKGROUND OF THE INVENTION

The present invention relates to an ultrasonic nondestructive test apparatus which detects changes in the velocity of the ultrasonic wave propagating in an object to be tested by interferometry.

The ultrasonic measurement method which utilizes the principle of interference is conventionally known as a method for measuring the velocity of sound in a liquid or a gas with precision. The method for causing interference is roughly classified into the method for varying the frequency of the ultrasonic waves and the method for varying the length of a propagation path of ultrasonic waves. An ultrasonic nondestructive test apparatus is known which utilizes this method for varying the length of the propagation path of ultrasonic waves. In this apparatus, an ultrasonic transmitter-receiver is arranged at the bottom of a vessel. A continuous electric signal generated by a high-frequency oscillator having an oscillating frequency of f is modulated into a high-frequency pulse signal by a pulse modulator. The high-frequency pulse signal thus obtained is applied to the transmitter-receiver in order to generate pulsed ultrasonic waves into a sample liquid as an object to be tested held in the vessel. The pulsed ultrasonic waves are reflected by a reflecting surface or a liquid surface of the sample liquid which is arranged in opposition to and parallel to the transmitter-receiver and are then returned to the transmitter-receiver.

In the ultrasonic nondestructive test apparatus as described above, the sample liquid is gradually discharged to gradually lower the liquid surface of the sample liquid, so that the length of the propagation path changes and maximum and minimum values of the amplitude of the reflected pulsed ultrasonic waves are obtained due to the interference. Accordingly, if the changes in the length of the propagation path within the sample liquid are accurately measured, the velocity of sound in the sample liquid may be determined since the oscillation frequency f of the oscillator is given.

It is also possible to measure the velocity of ultrasonic waves propagating in the liquid by arranging a pair of a transmitter and a receiver with a distance therebetween in a sample liquid held in a vessel and varying the distance between the transmitter and the receiver.

However, in the conventional apparatus as described above, the changes in the distance between the transmitter-receiver and the sample liquid or between the transmitter and the receiver, that is, the changes in the length of the propagation path of the sound waves are small. Therefore, precise measurement of such small changes requires, skills and a long measurement time. Furthermore, since the ultrasonic transmitter-receiver generates plane waves, measurements of two-dimensional distribution of the velocity of sound in an object to be measured may not be performed.

SUMMARY OF THE INVENTION

It is, therefore, an object of the present invention to provide an ultrasonic nondestructive test apparatus which is capable of accurately measuring the velocity of sound in a sample liquid speedily.

In order to achieve the above and other objects of the present invention, there is provided an ultrasonic nondestructive test apparatus wherein a focused ultrasonic wave from a focusing ultrasonic transmitting element is radiated on an object to be tested, a change in an ultrasonic wave energy received inside the object is detected at a fine portion thereof by an ultrasonic receiving element, one of the focusing ultrasonic transmitting element and the ultrasonic receiving element is finely vibrated by a vibrator, an output from the ultrasonic receiving element is displayed by a cathode-ray tube, and horizontal sweep of the cathode-ray tube is performed in accordance with an output signal from a low-frequency oscillator for vibrating the vibrator.

DETAILED DESCRIPTION OF THE PREFERRED EMBODIMENTS

Figure 1:
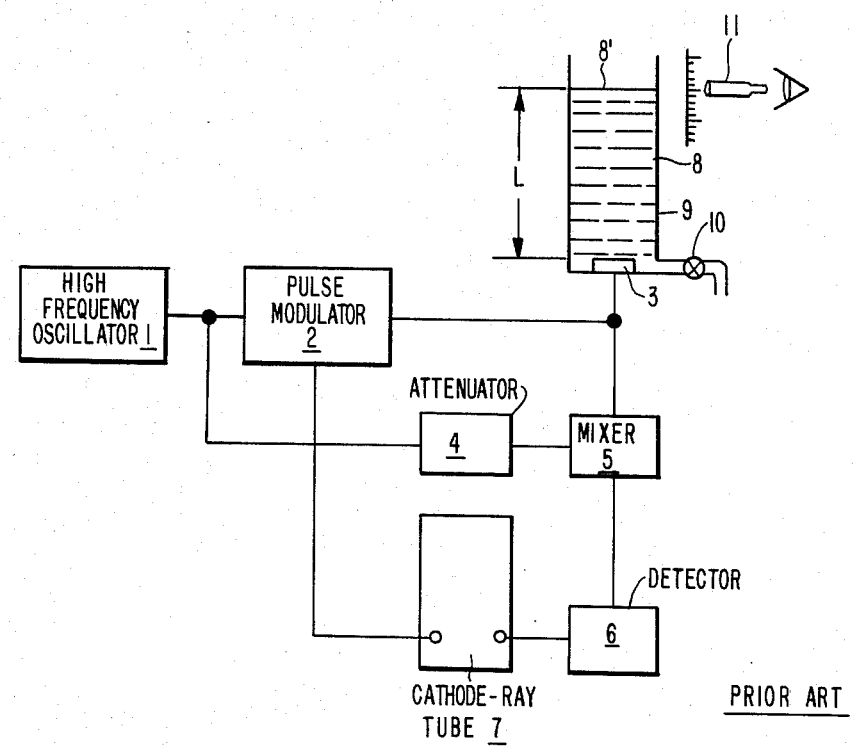
FIGS. 1 and 2 are block diagrams of conventional ultrasonic nondestructive test apparatuses.

A conventional ultrasonic nondestructive test apparatus will first be described with reference to FIG. 1. FIG. 1 shows a block diagram of an ultrasonic nondestructive test apparatus (Yoshimitsu Kikuchi and Daitaro Okuyama, Transactions at the Japanese Society of Acoustics, P. 181, February 1967) wherein the length of the propagation path of ultrasonic waves is varied. Referring to FIG. 1, reference numeral 1 denotes a high-frequency oscillator; 2, a pulse modulator; 3, a transmitter-receiver; 4, an attenuator; 5, a mixer; 6, a detector (rectifier); and 7, a cathode-ray tube (to be referred to as a CRT for brevity hereinafter). The transmitter-receiver 3 is mounted at the bottom of a vessel 9 holding a sample liquid 9. An outlet port 10 is arranged at the bottom of the vessel 9. A reading microscope 11 for measuring the level of the sample liquid 8 is arranged at the side surface of the vessel 9. A continuous electric signal generated by the high-frequency oscillator 1 of an oscillation frequency f is modulated into a high-frequency pulse signal by the pulse modulator 2. The high-frequency pulse signal is then applied to the transmitter-receiver 3 as an ultrasonic transducer to generate pulsed ultrasonic waves into the sample liquid 9 as an object to be measured. The pulsed ultrasonic waves are reflected by a reflecting surface which opposed and is parallel to the transmitter-receiver 3, or a liquid surface 8' of the sample liquid 8. The reflected pulsed ultrasonic waves are then supplied back to the transmitter-receiver 3, and are converted into an electric pulse signal. The electric pulse signal is supplied to the mixer 5 to be mixed with a reference signal part of the continuous electric signal generated by the high-frequency oscillator 1 which is adjusted in its amplitude by the attenuator 4. The composite signal from the mixer 5 is detected by the detector 6 and is displayed by the CRT 7. If the length 2L of the propagation path of ultrasonic waves is varied while maintaining the oscillation frequency f of the high-frequency oscillator 1 constant, the times of occurrence of the maximum and minimum values of the amplitude of the reflected pulse signal are repeatedly alternately displayed on the CRT 7 at every change in the length of the propagation path corresponding to every half wave length. In this conventional apparatus, the sample liquid 8 is gradually exhausted through the outlet port 10 arranged at the bottom of the vessel 9 holding the sample liquid 8 to thereby lower the level of the liquid surface 8'. If the magnitude of change in the level of the liquid surface 8' is read while the changes in the length of the propagation path which provide the occurrences of the maximum and minimum values of the amplitude of the reflected pulse waves are measured accurately, the velocity of sound in the sample liquid may be determined since the oscillation frequency f is known.

Figure 2:
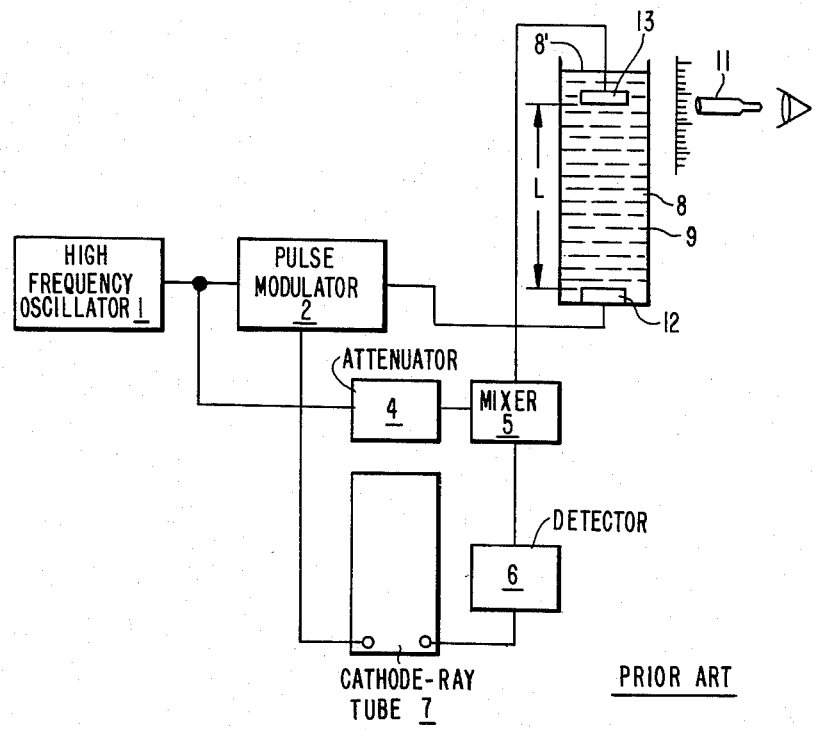

FIG. 2 is a block diagram of another conventional ultrasonic nondestructive test apparatus wherein the same reference numerals as in FIG. 1 denote the same parts. A transmitter 12 is connected to the pulse modulator 2, while a receiver 13 is connected to the mixer 5. The length of the propagation path which is defined by L between the transmitter 12 and the receiver 13 is varied, while the position of the lower surface of the receiver 13 is read by the reading microscope 11. The velocity of ultrasonic waves propagating in the liquid may thus be measured in the same manner as in the former conventional apparatus. However, in this conventional apparatus, the ultrasonic waves to be radiated into a liquid may be continuous waves and need not be pulsed ultrasonic waves.

In the conventional apparatuses as described above, changes in the length L between the transmitter-receiver 3 and the liquid surface 8' or between the transmitter 12 and the receiver 13, or changes in the length in the propagation path are small. Therefore, it is extremely difficult to measure such small changes. Measurement of such small changes requires skills and long time. Furthermore, since ultrasonic transducers for plane waves are used as a transmitter and a receiver, the two-dimensional distribution of the velocity of sound in the object may not be measured.

Figure 3:
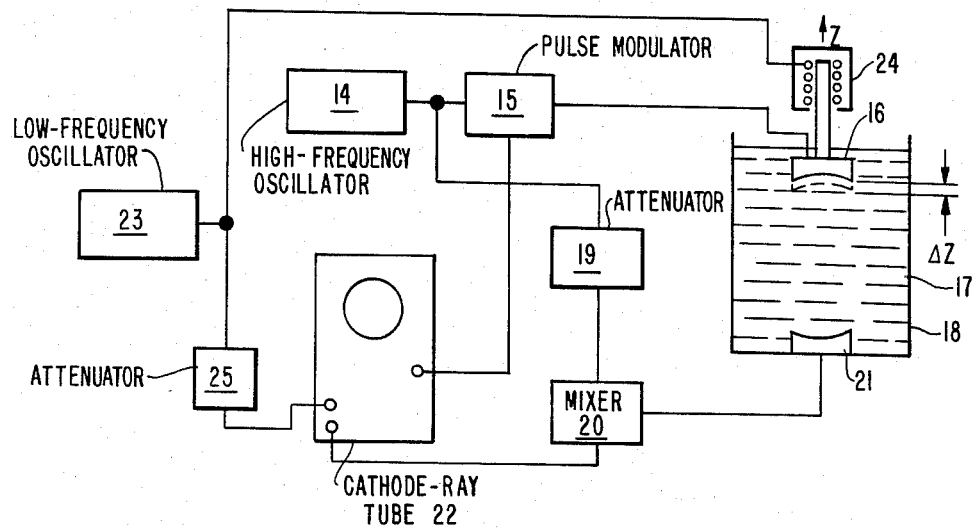
FIG. 3 is a block diagram of an ultrasonic nondestructive test apparatus according to an embodiment of the present invention.

The apparatus of the present invention eliminates the drawbacks of the conventional apparatus and allows accurate and fast measurement. An embodiment of the present invention will now be described with reference to FIG. 3. FIG. 3 shows a block diagram of an ultrasonic nondestructive test apparatus according to the first embodiment of the present invention. Referring to FIG. 3, reference numeral 14 denotes a high-frequency oscillator; 15, a pulse modulator; 16, a transmitter mounted at the top portion of a sample liquid 8 held in a vessel 17; 19, an attenuator; 20, a mixer; 21, a receiver arranged at the bottom of the vessel 17; 22, a CRT: 23, a low-frequency oscillator; 24, a vibrator for vibrating the transmitter 16; and 25, an attenuator for attenuating the low-frequency signal for vibrating the transmitter 16 to a predetermined level. The transmitter 16 and the receiver 21 comprise focusing ultrasonic transducers which have wide focal depths. The transmitter 16 and the receiver 21 are so arranged to have the common focal point. The vibrator 24 is connected to the transmitter 16 so as to finely change the distance between the transmitter 16 and the receiver 21 with good precision.

The mode of operation of the first embodiment of the present invention will now be described. Assume that the transmitter 16 is displaced by the vibrator 24 in the direction Z, and the amount of displacement $\Delta Z$ sinusoidally oscillates as a function of time t. In other words, $\Delta Z = A \sin \omega t$ where A is the maximum amplitude from a reference position, and $\omega$ is the angular frequency. Horizontal sweep of the CRT 22 is performed for B sin $\omega t$ in synchronism with the amount of displacement $\Delta Z$ of the transmitter 16. Meanwhile, the continuous electric signal generated by the high-frequency oscillator 14 is modulated by the pulse modulator 15 into a high-frequency pulse signal which is then applied to the receiver 16. Then, the pulsed ultrasonic waves are radiated into the sample liquid 17 and are transmitted to the receiver 21. The reference signal from the high-frequency oscillator 14 is adjusted by the attenuator 19 in its amplitude to have the same level as the transmitted signal received by the receiver 21. The reference signal is then mixed with the electric signal from the receiver 21 by the mixer 20. The composite signal, that is interference signal, from the mixer 20 is supplied to the CRT 22.

Figure 4:
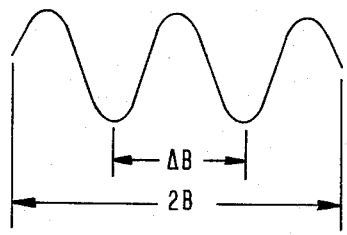
FIG. 4 shows a wave form with periodic maximum and minimum displayed on a cathode-ray tube.

Then, a waveform with periodic maximum and minimum values as shown in FIG. 4 is displayed on the screen of the CRT 22. Since the amplitude of the horizontal sweep of the CRT is B, the periodic changes in the length in the propagation path are multiplied by B/A. If the distance $\Delta B$ between the adjacent minimum values is measured on the screen of the CRT 22, the wavelength in the sample liquid is measured as $\Delta B \times (A/B)$. It is generally easy to set the ratio B/A to about 100 by optically measuring A or by calibrating in a medium such as water in which the velocity of sound is known. In this manner, if the frequency of the ultrasonic waves is represented by F, the velocity v of ultrasonic waves in the sample liquid 17 is given by:

$$v = F \times \Delta B \times (A/B)$$

An experiment conducted will now be described.

EXPERIMENT

Water was used as a sample liquid, and the frequency F of the ultrasonic waves was 2 MHz. The spatial amplitude A of the ultrasonic waves was 1 mm, while the angular frequency $\omega$ thereof was $2\pi \cdot 50$ Hz. Concave transducers having a depth of 1 mm or more as a transmitter and a receiver were opposed to each other to have a common focal point. Since the amplitude of horizontal sweep on the screen of the CRT was 5 cm, the ratio B/A was 50. The $\Delta B$ was measured to be 37.7 mm from the waveform as shown in FIG. 4. Therefore, the velocity v of sound is obtained as:

$$v = F \times \Delta B \times (A/B) = 2 \times 10^{-6} \times 37.7 \times 10^{-3} \times (1/50) = 1508 \text{ (m/sec)}$$

Figure 5:
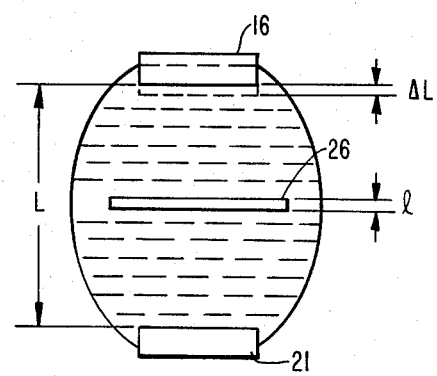
FIG. 5 shows one method for measuring the ultrasonic energy by interposing an object to be measured between a transmitter and a receiver.

If an object 26 which has the same velocity of sound as the sample liquid 17 and which has a uniform thickness is inserted in the sample liquid 17 between the transmitter 16 and the receiver 21, as shown in FIG. 5, in the ultrasonic nondestructive test apparatus of the embodiment shown in FIG. 3, the distance between the transmitter 16 and the receiver 21 which provides the maximum and minimum values of the composite wave displayed on the CRT 22 is slightly shifted from that for the sample liquid. Therefore, the amount of shift $\Delta L$ is given by:

$$\Delta L = l(1 - v_0/v_1)$$

where l is the thickness of the object 26 inserted, $v_1$ is the velocity of sound, and $v_0$ is the velocity of the sample liquid 17 which is measured in advance by the method described above. If the thickness l of the object 26 is given, the velocity $v_1$ may be calculated by substitution of it in:

$$v_1 = v_0/(1 - \Delta L/l)$$

However, it is not easy to accurately measure $\Delta L$.

Figure 6:
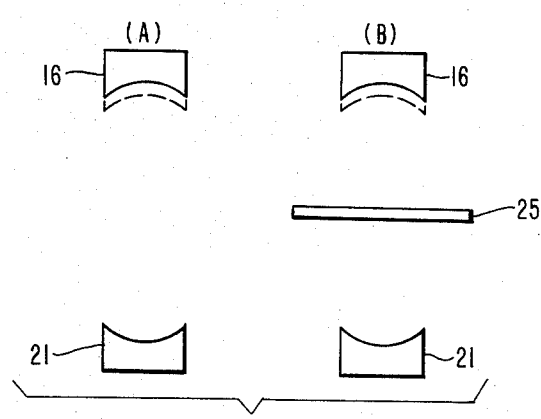
FIG. 6 is a view showing another method according to the present invention.
Figure 7:
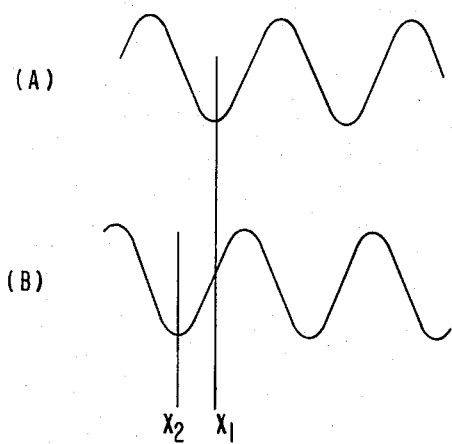
FIG. 7 shows a pattern displayed on the cathode-ray tube obtained with the method shown in FIG. 6.

According to the present invention, the amount of shift $\Delta L$ is easily measured by comparing, on the screen of the single CRT, the amounts of shift before and after the insertion of the object 26. More specifically, as shown in FIG. 6A, the transmitter 16 and the receiver 12 comprise focusing ultrasonic transducers and are arranged so that the ultrasonic waves propagate in the propagation path of the ultrasonic waves in the sample liquid as a reference medium. As in the embodiment described above, the waveform is displayed on the screen of the CRT 22 and is recorded by a memory scope or the like. Next, the transmitter 16 and the receiver 21 are moved to dispose the object 26 therebetween as shown in FIG. 6B, and a waveform is similarly displayed on the CRT 22. In the waveform as shown in FIG. 7A obtained with the propagation path which does not involve the object, the composite signal has the minimum value at a point $x_1$ where $\Delta Z = \Delta Z_1$. However, in the waveform shown in FIG. 7B obtained with the object 26, the composite signal does not have the minimum value at the point $x_1$ but at a point $x_2$. If the equipment is so set that the maximum and minimum values of the output on the x-axis (horizontal axis) of the CRT 22 are shifted to the left in FIG. 7, when the transmitter 16 is drawn closer to the receiver 21, the point $x_2$ of minimum value in FIG. 7B is shifted to the left of the point of minimum value in FIG. 7A, when the velocity of ultrasonic waves propagating through the object 26 is fast, and the point of minimum value is shifted to the right when the velocity of ultrasonic waves is slow. The $\Delta L$ may be determined by measuring the difference $\Delta x = x_1 - x_2$.

Figure 8:
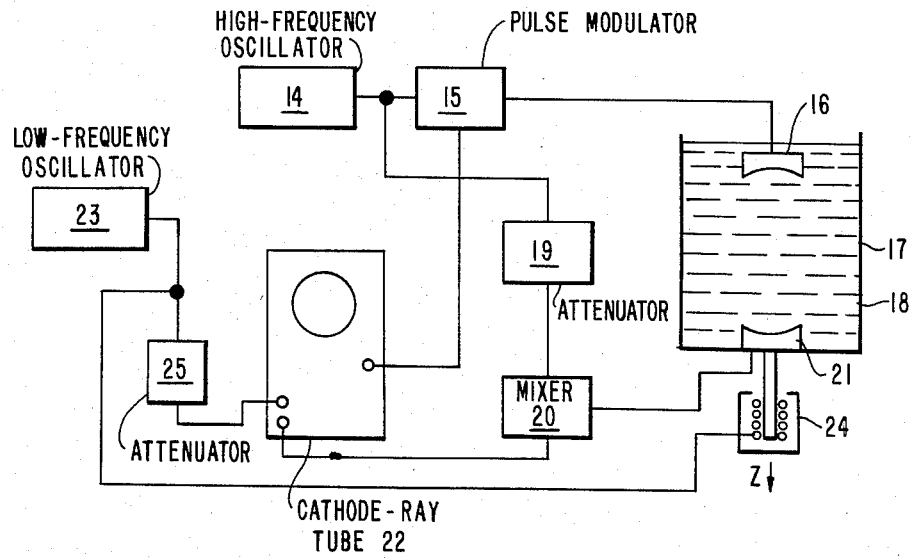
FIG. 8 is a block diagram of an ultrasonic nondestructive test apparatus according to another embodiment of the present invention.

FIG. 8 shows another embodiment of the present invention. The same reference numerals in FIG. 3 denote the same parts in FIG. 8. In FIG. 8, the vibrator 24 is only connected to the receiver 21. However, the mode of operation of the vibrator 24 is the same as that described with reference to FIG. 3, so a description thereof will be omitted.

In summary, according to the present invention, a transmitter or a receiver is vibrated by a vibrator. The ultrasonic beam propagating through the medium to be measured is scanned along the X-axis (horizontal axis) of the CRT in accordance with the low-frequency signal for driving the vibrator. Accordingly, the difference in the velocities of sound in different media may be easily seen from a display on the screen of the CRT, facilitating accurate measurement.

What is claimed is:

1. An ultrasonic nondestructive test apparatus for detecting variations in velocity of an ultrasonic wave propagating through an object, said apparatus comprising a focusing ultrasonic transmitting element for irradiating an object to be measured with a focused ultrasonic wave, an ultrasonic receiving element positioned with respect to said object for detecting ultrasonic energy from said transmitting element which has been subjected to a change inside the object, a low-frequency oscillator, a vibrator coupled to said oscillator for vibrating said ultrasonic transmitting element with a spatial amplitude which is small in comparison with the distance between said elements and at a frequency which is low compared to that of said ultrasonic wave, and a cathode-ray tube for displaying an output from said ultrasonic receiving element, the horizontal sweep of said cathode-ray tube being synchronized with an output signal from said low-frequency oscillator used for vibrating said vibrator, so that the display shows variations in the ultrasonic propagation velocity through said object.

2. An apparatus according to claim 1, wherein said object is immersed in a liquid medium, and a difference in velocities of the focused ultrasonic wave propagating in the object and the liquid medium is displayed on said cathode-ray tube.

3. An apparatus according to claim 1, wherein said object is a liquid medium.

4. An ultrasonic nondestructive test apparatus for detecting variations in velocity of an ultrasonic wave propagating through an object, said apparatus comprising a focusing ultrasonic transmitting element for irradiating an object to be measured with a focused ultrasonic wave, an ultrasonic receiving element positioned with respect to said object for detecting ultrasonic energy from said transmitting element which has been subjected to a change inside the object, a low-frequency oscillator, a vibrator coupled to said oscillator for vibrating said ultrasonic receiving element with a spatial amplitude which is small in comparison with the distance between said elements and at a frequency which is low compared to that of said ultrasonic wave, and a cathode-ray tube for displaying an output from said ultrasonic receiving element, the horizontal sweep of said cathode-ray tube being synchronized with an output signal from said low-frequency oscillator used for vibrating said vibrator, so that the display shows variations in the ultrasonic propagation velocity through said object.

5. An apparatus according to claim 4, wherein said object is immersed in a liquid medium, and a difference in velocities of the focused ultrasonic wave propagating in the objects and the liquid medium is displayed on said cathode-ray tube.

6. An apparatus according to claim 4, wherein said object is a liquid medium.

* * * * *